United States Patent
Schweizer

(10) Patent No.: US 8,600,001 B2
(45) Date of Patent: Dec. 3, 2013

(54) IMAGING FLUOROSCOPY METHOD AND SYSTEM USING A NAVIGATION SYSTEM MARKER DEVICE

(75) Inventor: Hans Schweizer, Plattling (DE)

(73) Assignee: Siemens Aktiengesellschaft, Munich (DE)

( * ) Notice: Subject to any disclaimer, the term of this patent is extended or adjusted under 35 U.S.C. 154(b) by 267 days.

(21) Appl. No.: 13/087,567

(22) Filed: Apr. 15, 2011

(65) Prior Publication Data

US 2011/0255661 A1 Oct. 20, 2011

(30) Foreign Application Priority Data

Apr. 20, 2010 (DE) .......................... 10 2010 015 633

(51) Int. Cl.
 *A61B 6/00* (2006.01)
(52) U.S. Cl.
 USPC .............. 378/42; 378/115; 378/205; 378/207
(58) Field of Classification Search
 USPC ...................... 378/42, 98, 114, 115, 205, 207
 See application file for complete search history.

(56) References Cited

U.S. PATENT DOCUMENTS

| | | | |
|---|---|---|---|
| 2006/0142656 A1* | 6/2006 | Malackowski et al. | ........ 600/424 |
| 2008/0031414 A1* | 2/2008 | Coppens | .......................... 378/65 |
| 2008/0200926 A1 | 8/2008 | Verard et al. | |
| 2008/0275334 A1 | 11/2008 | Berting | |
| 2008/0312530 A1 | 12/2008 | Malackowski et al. | |
| 2010/0041985 A1 | 2/2010 | Simon et al. | |

* cited by examiner

*Primary Examiner* — Glen Kao
(74) *Attorney, Agent, or Firm* — Schiff Hardin LLP

(57) ABSTRACT

In a method and system for use of a marker device in a fluoroscopy imaging system that is coupled with a navigation system, the navigation system is designed to determine a position of a patient, or of an instrument relative to the fluoroscopy system, with the use of a marker device that may be attached to the fluoroscopy system, and it is automatically detected whether the marker device is attached to the fluoroscopy system, and if so, information is automatically read out from the marker device, setting data are automatically determined depending on the information, and the fluoroscopy system is adjusted using the setting data such that an association between data acquired by the fluoroscopy system and data acquired by the navigation system is provided using the marker device attached to the fluoroscopy system.

12 Claims, 3 Drawing Sheets

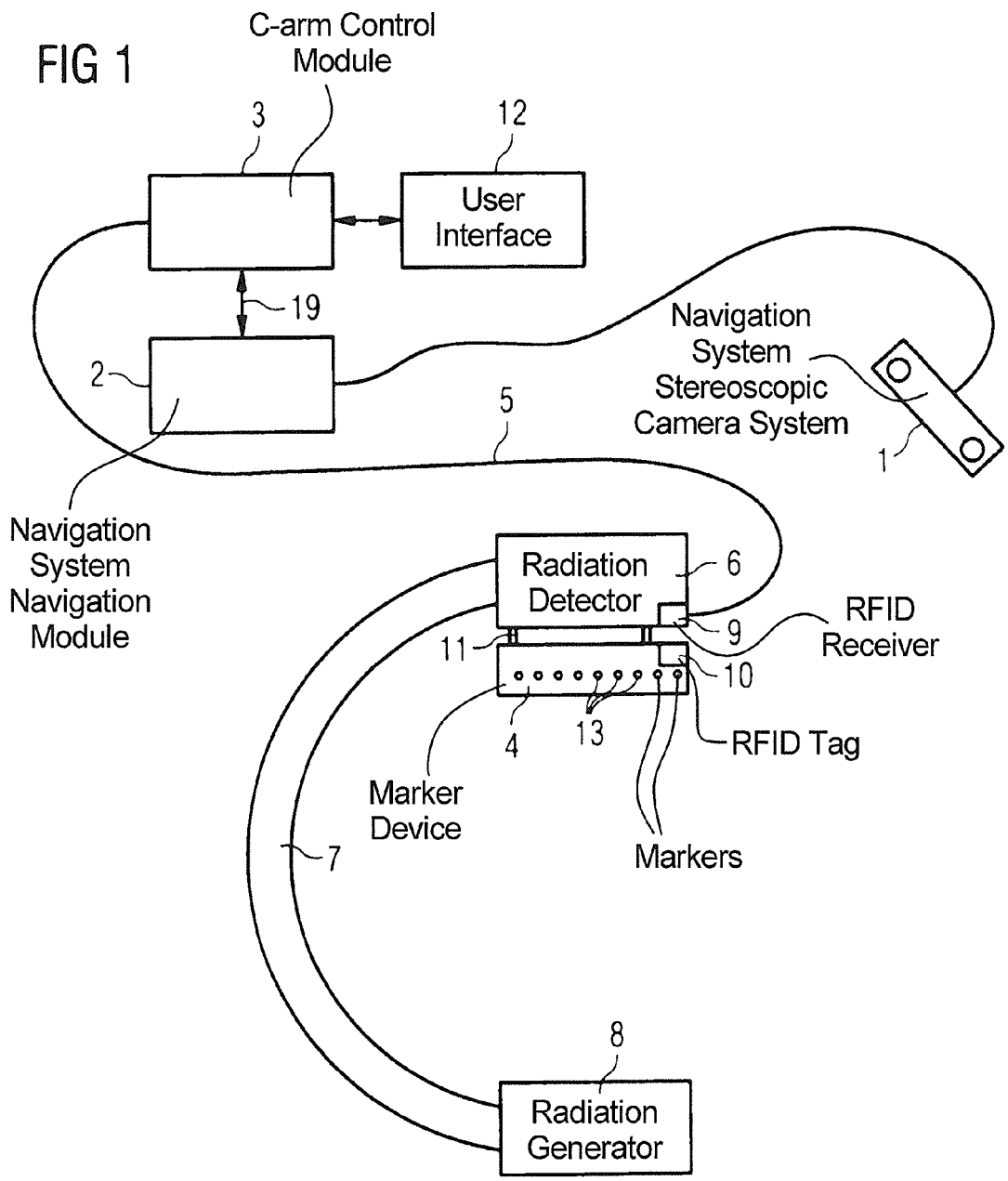

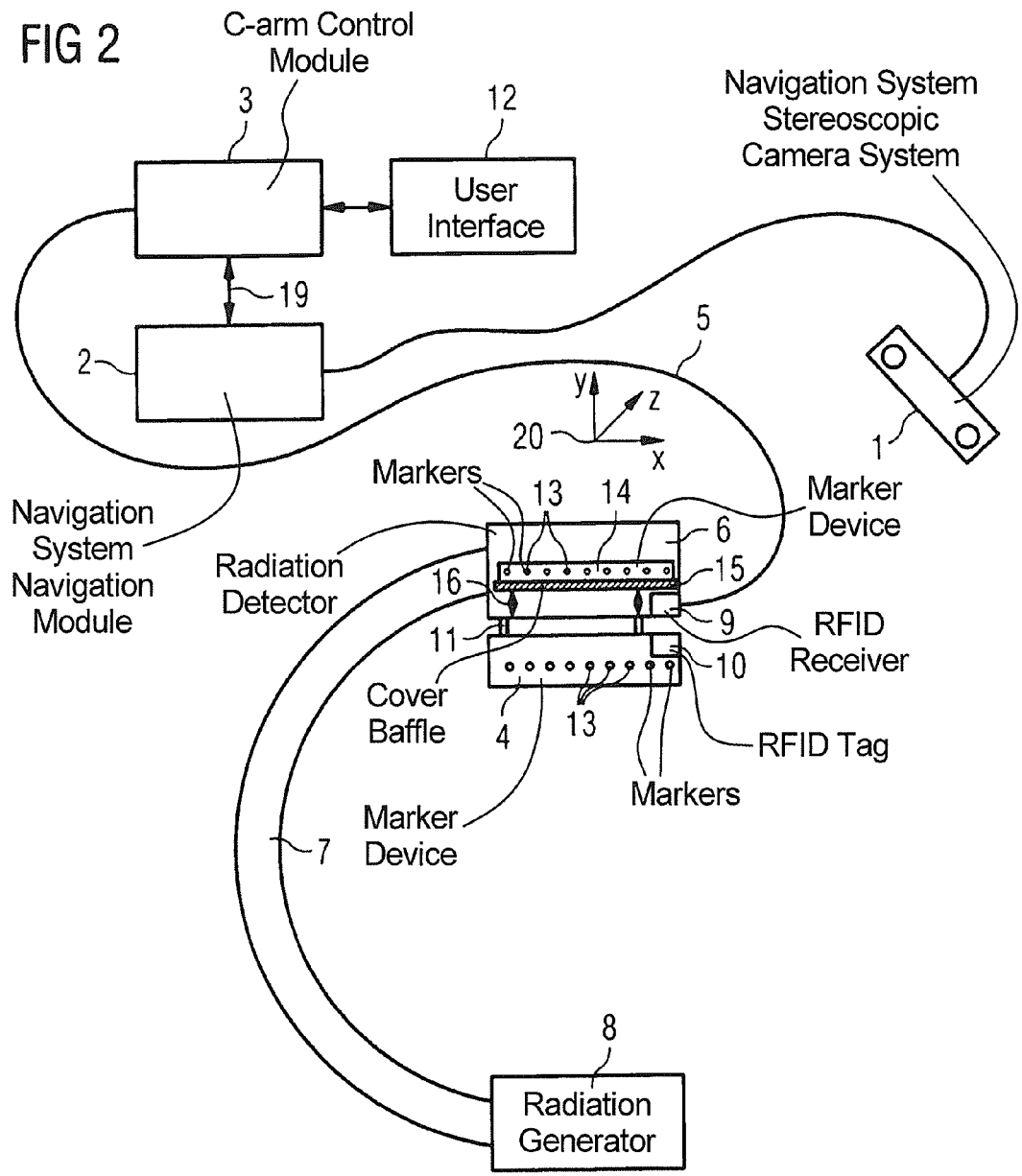

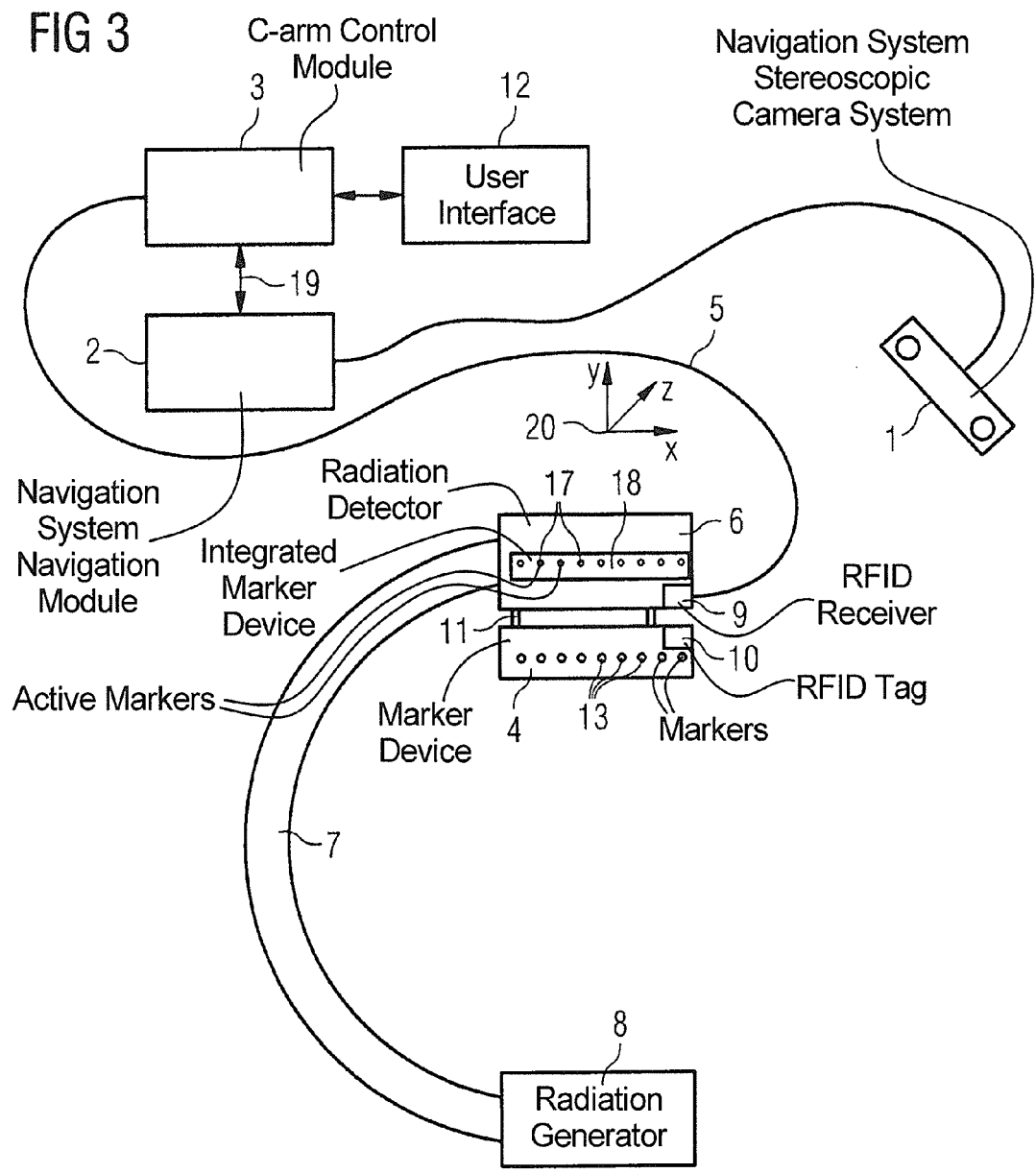

IMAGING FLUOROSCOPY METHOD AND SYSTEM USING A NAVIGATION SYSTEM MARKER DEVICE

BACKGROUND OF THE INVENTION

1. Field of the Invention

The present invention concerns a method in order to attach a marker device to an fluoroscopy imaging system (for example an x-ray system) and use it in fluoroscopy imaging. Moreover, the present invention concerns a corresponding marker device, a corresponding fluoroscopy imaging system, and a system that includes both the marker device and the fluoroscopy imaging system.

2. Description of the Prior Art

For the interaction of a fluoroscopy system (for example a C-arm x-ray system) with an optical navigation system, it is necessary (particularly for three-dimensional imaging) for a special marker device or marker geometry (normally a ring-like structure) to be attached to the fluoroscopy system, in particular to the image detector or to the radiation generator of the fluoroscopy system. This marker geometry is formed by multiple active or passive (inactive) markers that are arranged relative to one another in a specifically defined and unique three-dimensional pattern. For example, the active markers can be light-emitting diodes that emit in the infrared spectrum, and the passive markers can be spheres that are reflective in the infrared spectrum.

With the use of this marker geometry, an optical, stereoscopic tracking system or navigation system can unambiguously determine the position in space of the fluoroscopy system (in particular the C-arm) relative to the patient. With the use of previously generated calibration data (with which the weight of the marker device relative to the C-arm is compensated, for example), the unambiguous association of data determined by the fluoroscopy system (for example x-ray data) and navigation data determined by the navigation system is possible with regard to a specific patient. As part of the navigation system, a tracking system usually includes two cameras (or a stereoscopic camera system) and delivers three-dimensional data to the navigation system.

Newer developments in fluoroscopy systems enable marker rings of different manufacturers of navigation systems to be used with the same fluoroscopy system or C-arm. However, an exchange of this marker ring or this marker device involves significant manual effort. Moreover, in addition to the required mechanical reassembly tasks, manual adaptations of the operating software (for example the use of different calibration matrices) of the fluoroscopy system and of the respective navigation system are necessary.

Moreover, fluoroscopy systems are possible that have an integrated marker geometry. If a navigation system of a different manufacturer—and therefore a different marker geometry—is used in such a fluoroscopy system, removal of the integrated marker geometry before use is nearly impossible. This leads to problems in the detection of the marker geometry by the navigation system that is actually used, since henceforth two different marker geometries (the integrated and the newly applied) are located in the field of view of the tracking system (stereoscopic camera), which leads to incorrect detections.

SUMMARY OF THE INVENTION

An object of the present invention is to use a nearly arbitrary navigation system in a fluoroscopy system, wherein the problems stated above that are known according to the prior art are at least reduced.

In accordance with the present invention, a method is provided for use of a marker device in an fluoroscopy imaging system (for example x-ray system). The fluoroscopy system is coupled or connected with a navigation system. The navigation system is fashioned to determine a position of a patient or an instrument relative to the fluoroscopy system with the use of a marker device that is attached to the fluoroscopy system. The method according to the invention includes the following steps:

Automatic detection that the marker device is attached to the fluoroscopy system. For example, the automatic detection can be implemented by a device which must necessarily be activated when the marker device is attached to the fluoroscopy system. Moreover, it is possible for the marker device to emit specific radio waves that are detected by the fluoroscopy system as soon as the marker device is located in proximity to the fluoroscopy system.

Automatic readout of information from the marker device.

Automatic detection of setting data that are detected dependent on the information or with the use of the information directly. The fluoroscopy system can thereby be adjusted with the setting data such that a spatially precise association between data (for example x-ray data that are acquired by the fluoroscopy system) and navigation data (that are acquired by the navigation system) is possible by means of the marker device attached to the fluoroscopy system.

Adjustment of the fluoroscopy system depending on the setting data.

Since the method according to the invention automatically detects when a new marker device is attached to the fluoroscopy system, and based on this automatically determines the required setting data and adjusts the fluoroscopy system using the setting data such that it is adapted to the new marker device (and therefore to the new navigation system), the use of a new marker device—and therefore of a new navigation system—for a fluoroscopy system is significantly simpler than is the case according to the prior art. In other words, the adaptations in the operating software (for example application of different calibration matrices) of the fluoroscopy system can also be implemented automatically with regard to the navigation system coupled with it.

There are a number of possibilities for the automatic detection of the setting data depending on the information.

The actual information can be used as the setting data. In this case the setting data are read directly from the marker device.

The setting data can be sought and read out in a memory of the fluoroscopy system using the information read from the marker device. In this case the type of attached marker device is defined using the information, and via the type the setting data corresponding to this type are read out from the memory of the fluoroscopy system. In this variant, setting data for multiple types of marker devices may accordingly be stored in the memory of the fluoroscopy system.

The setting data embodies all necessary software settings, for example the corresponding calibration data and the settings of the corresponding navigation system in the user interface of the fluoroscopy system.

If an additional marker device already exists on the fluoroscopy system at the point in time at which the marker device is attached to the fluoroscopy system, there are the following possibilities:

If the additional marker device which can be attached to the fluoroscopy system or can be fashioned to be integrated with the fluoroscopy system comprises active markers, these are automatically deactivated as soon as it is detected that the marker device is attached to the fluoroscopy system.

Due to the deactivation of the active markers, these markers no longer interfere with the new navigation system. In other words, the new navigation system sees only the marker device that was just attached and advantageously no longer sees the additional marker device.

If the additional marker device includes inactive markers, these are covered automatically as soon as it is detected that the marker device is attached to the fluoroscopy system.

Due to this coverage of the inactive markers, these inactive markers do not disrupt the new navigation system. Similar to as in the previous case, the new navigation system sees only the marker device that was just attached and advantageously no longer sees the additional marker device.

Within the scope of the present invention, a marker device is also provided for an fluoroscopy imaging system. The marker device is designed such that it can be attached to the fluoroscopy system. With the aid of a navigation system coupled with the fluoroscopy system, the marker device enables the spatially precise determination of a position of a patient or of an instrument relative to the fluoroscopy system. The marker device includes a memory in which information is stored. With the use of this information, setting data can be determined with which the fluoroscopy system can be adjusted corresponding to the coupled navigation system and the marker device. Via the setting data, an association between data acquired by the fluoroscopy system and data acquired by the navigation system is provided using the marker device attached to the fluoroscopy system.

The memory of the marker device can be an RFID tag ("Radio-Frequency IDentification"). The RFID tag is a transponder which is supplied with energy by a reader device (which in particular is located on or in the fluoroscopy system) when the reader is located in sufficient proximity to the RFID tag.

If each marker device is designed with a wireless RFID tag in which all necessary information (for example manufacturer, type of navigation system) is stored which describes the marker device unambiguously in terms of its properties, the adaptation of the fluoroscopy system to the respective attached marker device can advantageously take place automatically.

Within the scope of the present invention, an fluoroscopy imaging system (for example an x-ray system with three-dimensional imaging) is also provided. The fluoroscopy system is coupled with a navigation system with which the position of a patient or of an instrument can be determined in relation to the fluoroscopy system with a marker device that can be attached to the fluoroscopy system. The fluoroscopy system also includes a reader device. Information is read from a memory of the marker device (for example from an RFID tag of the marker device) with the aid of this reader. Via this information the fluoroscopy system is in the position to locate and load corresponding setting data of the fluoroscopy system, meaning that the fluoroscopy system makes adjustments to the fluoroscopy system corresponding to the setting data. Through these adjustments the fluoroscopy system is set such that an association between data (for example x-ray data) acquired by the fluoroscopy system and data (navigation data) acquired by the navigation system is provided using the marker device, such that the data acquired by the fluoroscopy system have a spatial relationship with the fluoroscopy system, and therefore with the patient or the instrument.

The advantages of the fluoroscopy system according to the invention essentially correspond to the advantages of the method according to the invention which have been stated in detail in the preceding, such that here a repetition is omitted.

The following possibilities according to the invention exist to locate the setting data using the information from the marker device:

According to a first possibility, the setting data for specific (or all) marker devices usable with the corresponding fluoroscopy system are stored in a memory (for example a database) of the fluoroscopy system. Using the information read from the memory of the marker device, the setting data required for the corresponding marker device attached to the fluoroscopy system can be discovered and loaded in the memory of the fluoroscopy system. For example, for this purpose the information can comprise a corresponding identification of the marker device or the type of marker device, such that using the identification or, respectively, the type the correct setting data required for the marker device can be located in the memory of the fluoroscopy system. In other words, the setting data stored in the memory of the fluoroscopy system for the different marker devices offer the possibility to discover the corresponding setting data using the identification or, respectively, the type of attached marker device. For example, for this purpose the setting data can comprise an identification or a type of marker device for which the corresponding setting data apply, such that the setting data in the memory of the fluoroscopy system can be located using the identification or, respectively, the type of setting data.

According to the second possibility, the information itself is used as the setting data. In other words, according to the second possibility the setting data are read directly from the memory of the marker device.

Naturally, hybrids of the first and second possibility are also conceivable. The information stored in the memory of the marker device thereby on the one hand comprises the identification or the type of the corresponding marker device and on the other hand comprise a portion of the setting data. As in the first possibility, the remaining setting data are stored in the memory of the fluoroscopy system and are found via the identification data or the type.

The following embodiments of the present invention are concerned with a deactivation of a marker device already integrated with the fluoroscopy system or attached to the fluoroscopy system.

According to a first embodiment, an additional marker device integrated with the fluoroscopy system or marker device attached to the fluoroscopy system comprises active markers. The fluoroscopy system is designed to deactivate these active markers, in that the fluoroscopy system interrupts an energy feed to the active markers, for example.

Due to the deactivation of the active markers of the additional marker device, this additional marker device can essentially be taken out of operation so that the navigation system only still detects the markers of the new marker device attached to the fluoroscopy system and is no longer disrupted by the markers of the additional marker device.

Additional manual processes to deactivate the additional marker device are advantageously spared via the automatic deactivation of the additional marker device.

According to a second embodiment of the invention, the additional marker device integrated with the fluoroscopy system or attached to the fluoroscopy system comprises inactive markers. In this embodiment, the fluoroscopy system comprises a baffle with which the inactive markers can be completely covered with regard to cameras of the optical tracking system.

Since the inactive markers of the additional marker device are covered with the baffle such that they can no longer be detected by the camera or cameras of the optical tracking system, the navigation system still "sees" only the markers of the marker device newly attached to the fluoroscopy system, such that the navigation system is no longer disrupted by the markers of the additional marker device.

The fluoroscopy system can include a motor with which the baffle can be moved automatically such that the inactive markers can no longer be detected by the navigation system.

The covering of the inactive markers of the additional marker device is additionally facilitated by the motor.

Moreover, the fluoroscopy system can be designed such that it moves the baffle automatically with the aid of the motor such that the inactive markers are covered with regard to the navigation system when the fluoroscopy system detects that the new marker device is attached to the fluoroscopy system.

Similar to as in the corresponding variant of the first embodiment according to the invention, this variant of the second embodiment according to the invention ensures that no manual handling by an operator is needed, that the inactive markers of the additional marker device are essentially taken out of operation when the new marker device is detected by the fluoroscopy system.

It is noted that the detection of the new marker device can be realized by the fluoroscopy system in that the reader of the fluoroscopy system reads the information from the memory of the new marker device.

Moreover, it is noted that, according to the invention, it would also be possible to realize a fluoroscopy system which has no reader but nevertheless is designed to deactivate active markers (see first embodiment) or to mask inactive markers (see second embodiment). In this case an operator could initiate the deactivation of the active markers or the masking of the inactive markers when the new marker device is attached.

Finally, within the scope of the present invention a system is provided which comprises a marker device according to the invention and a fluoroscopy system according to the invention. Such a system could also include the navigation system coupled with the fluoroscopy system.

The present invention is particularly suitable for imaging x-ray systems that can cooperate with different marker devices or navigation systems. Naturally, the present invention is not limited to this preferred application field since the present invention can also be used in fluoroscopy systems operating with reflections (for example sonography) or in other systems operating with fluoroscopy.

BRIEF DESCRIPTION OF THE DRAWINGS

FIG. 1 shows an embodiment of an x-ray system according to the invention.

FIG. 2 shows an additional embodiment of an x-ray system according to the invention with an integrated marker device with inactive markers.

FIG. 3 shows another embodiment of an x-ray system according to the invention with an integrated marker device with active markers.

DESCRIPTION OF THE PREFERRED EMBODIMENTS

An x-ray system according to the invention is shown in FIG. 1. The x-ray system according to the invention has a C-arm 7 at which a radiation generator 8 and a detector 6 are mounted. A patient to be examined is arranged by the x-ray system between the radiation generator 8 and the detector 6 so that the radiation emitted by the radiation generator 8 irradiates the patient and then is detected by the detector 6. An external marker geometry or marker device 4 can be attached to the detector 6 by means of a mechanical fastener. Another preferred location to fasten the marker geometry 4 is the radiation generator 8; however, other fastening locations are also conceivable as long as an unambiguous spatial association is enabled between marker geometry and acquired image data. This is in particular the case when the marker geometry is located within the emitted radiation.

For example, the external marker device 4 can include multiple spherical active or inactive markers 13 and an RFID tag 10 in which are stored information that unambiguously describes the type of the marker device 4. The markers 13 can also be hemispheres or what are known as surface markers which are fashioned as a flat, reflective circle. With the use of the markers 13, the position of the C-arm 7 in space relative to a patient or to an instrument which is used for operation on the patient can be unambiguously determined with a stereoscopic camera system 1 of a navigation system that is coupled with the x-ray system.

The information in the RFID tag 10 is read with the aid of an RFID receiver 9 of the detector 6 as soon as a distance between the external marker device 4 and the detector 6 is small enough that this information or data can be wirelessly detected by the RFID receiver.

This information is transferred to a C-arm control module 3 of the x-ray system via a data interface 5. The C-arm control module 3 is connected with a user interface 12 and with a navigation module 2 of the navigation system, wherein the stereoscopic camera system 1 is connected with the navigation module 2 via a data interface and supplies the navigation module 2 with position data of all detected markers 13, wherein the position data are additionally processed in the navigation module 2. A data exchange between the navigation system and the x-ray system in particular occurs via the shown interface 19 between the C-arm control module and the navigation module 2.

The C-arm control module 3 has a local database in which are stored all necessary settings (for example calibration matrices, pre-selection of the correct navigation system in the user interface) for multiple marker devices. Using the information in the RFID tag 10, the necessary (software) settings are determined and implemented for the current marker device attached to the x-ray system. A manual intervention by a service technician or by an operator is no longer necessary.

However, it is also possible that the setting data are read from the RFID tag 10. For example, in a first step the x-ray system thereby reads a specific type of the marker device 4 from the RFID tag 10 via the RFID receiver 9. In the next step, the specific data which are necessary to operate the marker device 4 with the x-ray system (in particular the C-arm 7)—for example calibration matrices—are read out from the RFID tag 10. If all necessary data are known, everything that is necessary can be set automatically (for example in the user interface 12) so that an operator (for example a physician) has only to connect the navigation system with the x-ray system and conduct a three-dimensional scan. The rest—thus the transfer of the volume data to the navigation system—takes place wholly automatically, for example.

An additional x-ray system according to the invention is shown in FIG. 2 with an integrated internal marker geometry or marker device 14. The additional x-ray system according to the invention of FIG. 2 has significant similarities to the x-ray system according to the invention from FIG. 1, such that only the differences are discussed in the following.

In order for the navigation system consisting of the navigation module 2 and the stereoscopic camera 1 to operate correctly with the newly attached marker device 4, the integrated marker device 14 for the navigation system—in particular for the stereoscopic camera 1—must be taken out of operation beforehand. Since the integrated marker device 14 comprises inactive markers 13 (for example marker spheres reflecting in the infrared spectrum), these inactive markers 13 are covered by means of a motorized, movable cover baffle 15 and therefore are removed from the field of view of the stereoscopic camera 1. Alternatively, the cover baffle 15 can also be shifted via a purely mechanical design (for example by means of a slide rod) without the assistance of a motorized movement unit as soon as the marker device 4 has been correctly mechanically arrested. In FIG. 2 the cover baffle 15 is shifted in the y-direction (see coordinate system 20) over the integrated marker device 14 via a displacement mechanism 16 in order to cover said integrated marker device 14.

A different x-ray system according to the invention is shown in FIG. 3, which x-ray system is similar to the x-ray system shown in FIGS. 1 and 2, such that only the differences relative to the x-ray system shown in FIG. 3 are discussed.

In contrast to the x-ray system shown in FIG. 2, the x-ray system shown in FIG. 3 comprises an integrated marker device 18 with active markers 17 (for example infrared LEDs). As soon as the x-ray system detects the RFID tag 10 of the newly attached marker device 4 via its RFID receiver 9, said x-ray system deactivates the active markers 17. For example, in that the voltage of the active infrared LEDs is deactivated, these are invisible to the stereoscopic camera 1 of the navigation system and can no longer cause any interference effects with regard to the newly attached marker device 4.

Although modifications and changes may be suggested by those skilled in the art, it is the intention of the inventor to embody within the patent warranted hereon all changes and modifications as reasonably and properly come within the scope of his contribution to the art.

I claim as my invention:

1. A method for adjusting a fluoroscopy system, comprising the steps of:
   with a detector connected to a computerized processor, detecting whether a marker device of a navigation system is attached to a fluoroscopy system, said marker device being configured for use by said navigation system to identify a position of a patient or an instrument relative to the fluoroscopy system;
   providing an input from the detector to said computerized processor that said marker device has been detected attached to the fluoroscopy system;
   after detection that said marker device is attached to the fluoroscopy system, automatically reading out information from the marker device and supplying said information to said processor;
   in said processor, automatically determining setting data dependent on said information, said setting data designating a spatial relationship between data acquired by the fluoroscopy system and data acquired by the navigation system; and
   from said processor, automatically adjusting a spatial position of the fluoroscopy system using said setting data.

2. A method as claimed in claim 1 comprising reading out information from the marker device that comprises said setting data.

3. A method as claimed in claim 1 comprising storing said setting data in a memory accessible by said processor, and reading out said setting data from said memory dependent on the information read out from said marker device.

4. A method as claimed in claim 1 wherein said marker device is a first marker device, and detecting, with said detector, a presence of a second marker device attached to or integrated in said fluoroscopy system, and automatically electronically deactivating said second marker device when said first marker device is detected.

5. A method as claimed in claim 1 wherein said marker device is a first marker device, and detecting, with said detector, a presence of a second marker device attached to or integrated in said fluoroscopy system, and automatically covering said second marker device when said first marker device is detected.

6. A marker device for an imaging fluoroscopy system comprising:
   a fastener that mechanically attaches the marker device to a component of a fluoroscopy system;
   a position indicator detectable by a navigation system to allow determination of a position of a patient or an instrument relative to the fluoroscopy system; and
   a memory having information electronically stored therein allowing setting data to be determined dependent on said information, said setting data allowing adjustment of a position of at least one component of the fluoroscopy system.

7. A marker as claimed in claim 6 wherein said memory is an RFID tag.

8. A fluoroscopy system, comprising:
   a fluoroscopy imaging apparatus;
   a detector that detects whether a marker device of a navigation system is attached to a component of the fluoroscopy apparatus, said marker device being configured for use by said navigation system to identify a position of a patient or an instrument relative to the fluoroscopy system;
   a computerized processor that receives an input from the detector indicating said marker device has been detected attached to the fluoroscopy system;
   after detection that said marker device is attached to the fluoroscopy system, a readout unit that automatically reads out information from the marker device and supplies said information to said processor;
   said processor being configured to automatically determine setting data dependent on said information, said setting data designating a spatial relationship between data acquired by the fluoroscopy apparatus and data acquired by the navigation system; and
   said processor being configured to automatically adjust a spatial position of the fluoroscopy apparatus using said setting data.

9. A system as claimed in claim 8 wherein said readout unit reads out information from the marker device that comprises said setting data.

10. A system as claimed in claim 8 comprising a memory in which said setting data is stored so as to be accessible by said processor, and said processor being configured to read out said setting data from said memory dependent on the information read out from said marker device.

11. A system as claimed in claim 8 wherein said marker device is a first marker device, and wherein said detector detects a presence of a second marker device attached to or integrated in a component of said fluoroscopy apparatus, and wherein said processor is configured to automatically electronically deactivate said second marker device when said first marker device is detected.

12. A system as claimed in claim 8 wherein said marker device is a first marker device, and wherein said detector detects a presence of a second marker device attached to or integrated in a component of said fluoroscopy system, and wherein said processor is configured to automatically operate a baffle at said component to cover said second marker device when said first marker device is detected.

* * * * *